United States Patent [19]
Chaney

[11] Patent Number: 5,195,943
[45] Date of Patent: Mar. 23, 1993

[54] MALE ORGAN RESTRICTOR RING APPLICATOR

[76] Inventor: John L. Chaney, 156 Broad St., P.O. Box 790, Lake Geneva, Wis. 53147

[21] Appl. No.: 767,884

[22] Filed: Sep. 30, 1991

[51] Int. Cl.⁵ .............................. A61F 5/41
[52] U.S. Cl. .......................... 600/41; 600/38
[58] Field of Search ............... 600/38, 39, 41; 606/140, 141, 157

[56] References Cited

U.S. PATENT DOCUMENTS

| | | | |
|---|---|---|---|
| 2,874,698 | 2/1959 | Sell | 600/38 |
| 3,744,486 | 7/1973 | Wilson. | |
| 3,760,810 | 9/1973 | Van Hoorn | 606/140 |
| 4,539,980 | 9/1985 | Chaney. | |
| 4,735,194 | 4/1988 | Stiegmann | 606/140 |
| 4,753,227 | 6/1988 | Yanuck, Jr. | 600/41 |
| 4,856,498 | 8/1989 | Osbon. | |

Primary Examiner—Cary E. O'Connor
Attorney, Agent, or Firm—Fuller, Ryan, Hohenfeldt & Kees

[57] ABSTRACT

An elastic restrictor ring is transferred from the periphery of a vacuum cylinder into tight surrounding relationship to the base of a penis undergoing vacuum therapy by means of a sleeve on the cylinder contiguous with the restrictor ring. The sleeve is provided with a camming surface that reacts against a fixed cam element on the cylinder such that when the sleeve is rotated it is cammed axially toward the end of the vacuum cylinder in which case the restrictor ring is forced off of the cylinder and onto the base of the penis.

4 Claims, 3 Drawing Sheets

MALE ORGAN RESTRICTOR RING APPLICATOR

BACKGROUND OF THE INVENTION

The invention disclosed herein pertains generally to male impotency therapy and in particular to a device for transferring an elastic restrictor ring to the base of the penis when the penis extends into a vacuum cylinder which has been used to induce an erection.

Vacuum devices have been widely used to obtain an artificial erection by inducing flow of blood into the penis. After the erection is obtained as a result of the penis being exposed to negative pressure, an elastic ring or rubber band is slid off of the vacuum cylinder and onto the base of the penis to trap the blood in it. Vacuum devices for inducing an erection are described in several patents including U.S. Pat. Nos. 3,744,486 and 4,856,498. A typical vacuum erection inducing device comprises a cylinder that has one open end which can be slid over the flaccid penis with the rim of the cylinder pressed tightly against the body tissue in the pubic area surrounding the base of the penis. The force applied to the cylinder must be sufficient to effect a satisfactory vacuum seal. Concurrently with this condition being obtained, a vacuum pump is actuated to create a vacuum or negative pressure in the cylinder chamber. The differential between the subject's blood pressure and the negative pressure in the cylinder chamber results in arterial blood flowing into the penis with sufficient force to stiffen it. Before the negative pressure or vacuum can be relieved, it is necessary to apply a restrictor to the base of the penis for preventing outflow of venous blood and instantaneous loss of the erection. If a ring having appropriate elastic force is applied, the erection may be maintained for as much as thirty minutes after exposure to the vacuum environment is discontinued. It is customary for the restrictor to comprise a rubber band or elastic ring which is stretched to fit over the outside diameter of the cylinder at its distal end, that is, adjacent the end or rim of the vacuum cylinder which is pressed against the tissue in the pubic area to effect the vacuum seal. U.S. Pat. No. 4,539,980, issued to John L. Chaney on Sep. 10, 1985 depicts and describes a restrictor ring which is ideal for use in conjunction with a vacuum cylinder. The term restrictor ring as used herein is intended to be generic to rubber bands as well as rings or bands composed of other elastic materials.

When the vacuum cylinder is used to obtain an erection by a male who has firm tissue in the pubic area, the rim of the vacuum cylinder will only make a small annular dent in the tissue. As a result of this ideal condition, it is usually fairly easy to slide the restrictor ring off the distal end of the cylinder by use of the fingers on one or both of the hands. However, when the subject is obese or otherwise has poor muscle tone, the tissue in the pubic area is soft and easily distendible. In such case, when the rim of the cylinder is pressed against the tissue, the rim forms a deep annular groove in the tissue before a good enough seal is created to justify activating the vacuum inducing pump. At this time, of course, the restrictor ring will be stretched onto the outside of the vacuum cylinder in readiness for being pushed off and applied to the base of the penis when the desired vacuum and erection have been obtained. A serious problem may arise at this juncture in the cases where the tone of the tissue in the pubic area is poor. In such cases when the vacuum is created, the rim of the cylinder is drawn more deeply in the groove and tissue immediately surrounding the base of the penis is caused to extend as much as one and one-half inches in some cases into the vacuum tube. Now, before the restrictor ring can be pushed off the rim of the vacuum tube it is necessary for the male to get his fingers under the overlaying flabby tissue to push the ring off. This results in the finger tips digging into the tissue and is very painful for a user. The body tissue is often bruised such that colored spots, indicative of subcutaneous hemorrhaging, occur around the penis. The situation is aggravated in some cases as a result of the entanglement of the finger tips in the restrictor ring with the pubic hair. The seriousness of the problem can be inferred from reports by users that it may take them up to four minutes to get the ring applied to the base of the penis. They also report that during the restrictor ring transfer maneuver, the vacuum seal is sometimes broken in which case the erection is lost and the whole procedure has to be repeated.

The invention disclosed herein eliminates the problems just discussed.

SUMMARY OF THE INVENTION

According to the invention, the vacuum cylinder of a vacuum impotence therapy device is provided with a sleeve that fits concentrically over the outside diameter of the vacuum cylinder near its distal end. When the sleeve is axially retracted on the cylinder, space is provided on its outside diameter at its distal end for installing the stretched elastic restrictor ring. The sleeve is provided with an axially extending camming surface or riser at its end which is remote from the ring at the open penis admitting end of the cylinder. An abutment in the form of a stop member or stationary cam is formed or fastened on the outside diameter of the vacuum cylinder in a position such that when the sleeve is in a certain position of angular rotation on the cylinder, the sleeve can retract axially despite the stop or fixed cam. When the sleeve is rotated, and as a result of its configuration at the end remote from the elastic ring, the sleeve is forced axially toward the distal end of the cylinder, thereby pressing the restrictor ring off the cylinder and applying it to the base of the penis to maintain the erection after the vacuum is relieved and the penis is withdrawn.

How the foregoing features of the invention are implemented will now be described in greater detail in reference to the accompanying drawings.

DESCRIPTION OF A PREFERRED EMBODIMENT

Figure 1:
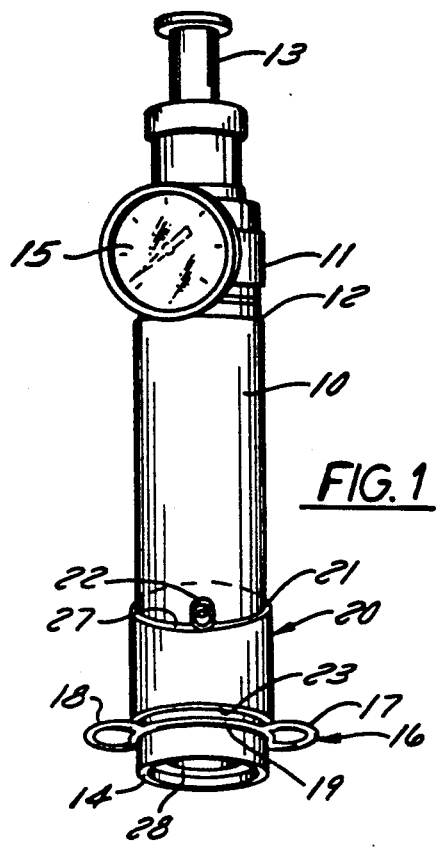
FIG. 1 is a perspective view of an illustrative vacuum type erection obtaining apparatus equipped with the new device for transferring a restrictor ring to the base of the penis.
Figure 7:
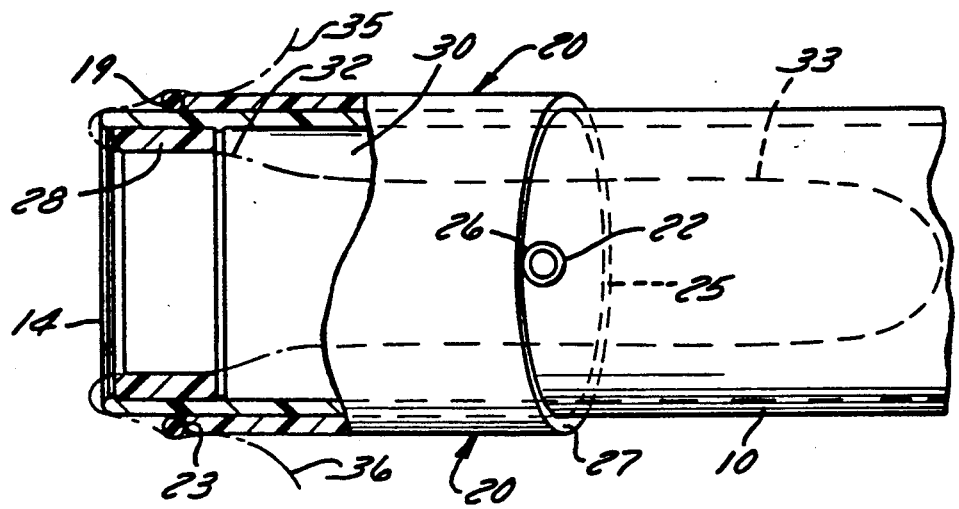
FIG. 7 depicts a fragment of the vacuum cylinder with the new restrictor ring applicator or transfer sleeve positioned in readiness for rotating it to push the restrictor ring off the cylinder.

FIG. 1 illustrates a popular type of apparatus for inducing an erection with the aid of vacuum. The device comprises a vacuum cylinder 10 which is preferably made of transparent plastic. By way of example and not limitation, this cylinder may have an outside diameter of approximately two inches. A vacuum pump 11 is mounted in vacuum tight relationship to the proximal end 12 of the pump vacuum cylinder. An axially reciprocable piston rod 13 extends from the pump body. Axial reciprocation of piston rod 13 results in a vacuum being created in the internal chamber of cylinder 10 if the rim 14 of the distal end of the cylinder is pressed against the tissue surrounding the penis which is projecting into the cylinder as depicted in FIG. 7, for example. A vacuum gauge 15 indicates to the user the degree of vacuum created in the chamber of cylinder 10. A vacuum corresponding to about ten inches of mercury or 250 mm of mercury is usually about right. A vacuum relief valve, not shown, is usually provided to limit the vacuum to a safe value. An elastic restrictor ring, generally designated by the numeral 16, of the type depicted in U.S. Pat. No. 4,539,980 to John L. Chaney by way of example, is installed on the outside diameter of the vacuum cylinder 10 near the distal rim 14 at the distal end of the cylinder. This particular restrictor ring has two finger engaging side loops 17 and 18 joined with the outside diameter of a central ring portion 19. Restrictor rings of this general type are often composed of natural or synthesized latex. In FIG. 1, the new rotatable restrictor ring transfer sleeve is generally designated by the numeral 20. Sleeve 20 is in the nature of a cylinder whose inside diameter fits slidably and rotatably on the outside diameter of vacuum cylinder 10 and has one end 21 cut off by a plane that has passed through the cylindrical sleeve at an angle with respect to the axis of the sleeve so as to produce an endwise presented cam surface 27. The cam surface 27 is positioned for reacting against a fixed cam or stop 22 such that when the sleeve 20 is rotated with cam surface 27 in contact with cam 22, the sleeve is driven axially toward the distal end 14 of the vacuum cylinder to thereby push restrictor ring 16 from the cylinder and onto the base of the penis.

Figure 2:
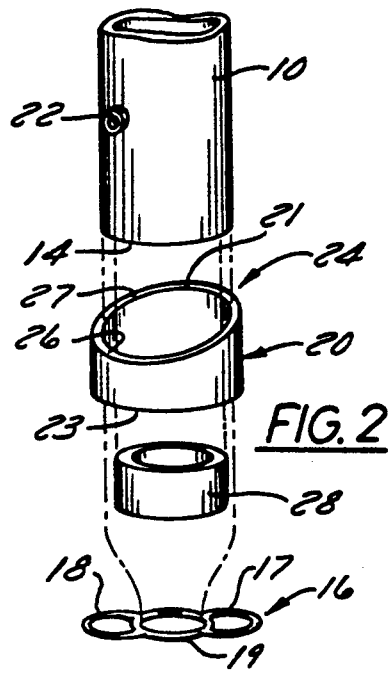
FIG. 2 is a fragmentary exploded view of the essential components of the new restrictor ring applicator or transferring device.

FIG. 2 depicts parts of the ring transfer device with greater clarity. A portion of evacuable cylinder 10 is shown. The stop or reaction cam 22 is preferably molded integrally with the cylinder 10 although it could be applied separately by using an adhesive. It is easy to see that the transfer sleeve 20 is terminated at its distal end in a rim 23 which is at a right angle relative to the axis of the cylindrical sleeve. In other words, the open end or rim 23 of sleeve 20 is square. The opposite end 24 of sleeve 20 is beveled as if it were formed by passing a plane through a cylinder at an angle relative to the axis of the cylinder. This results in the sleeve 20 having an axially long side 25 and a diametrically opposite axially extending short side 26. Thus, the end surface 27 of the sleeve constitutes a camming surface which can react against the stop or fixed cam 22 when the sleeve is rotated on the cylinder. This results in the cam sleeve being retracted from the distal end of the cylinder when the surface 27 on the short side 26 of the sleeve is in contact with cam 22 and in the sleeve being advanced toward the distal end 14 of the cylinder 10 when the sleeve is rotated such that its end surface 27 at the long side 25 of the sleeve is contiguous with the cam 22.

Figure 5:
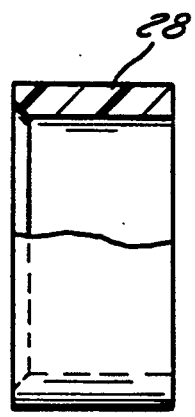
FIGS. 5 and 6 depict bushing rings, partly in section, which are inserted in the distal end of the vacuum cylinder, according to the invention, to accommodate penises having different diameters.
Figure 6:
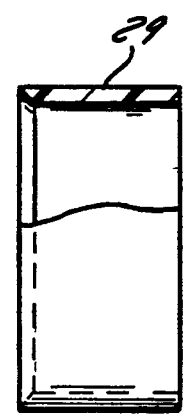

FIG. 2 also shows one of the penis diameter size adapters 28 aligned coaxially with the bore of vacuum cylinder 10 for being inserted therein. This size adapter 28 may be the one depicted in FIG. 5. Another size adapter 29 is shown in FIG. 6. It will be evident that its bore is larger than the adapter 28 depicted in FIG. 5.

FIG. 2 also shows the restrictor ring 16 before the central ring portion 19 thereof is stretched over the outside diameter of cylinder 10 near its distal end.

Figure 3:
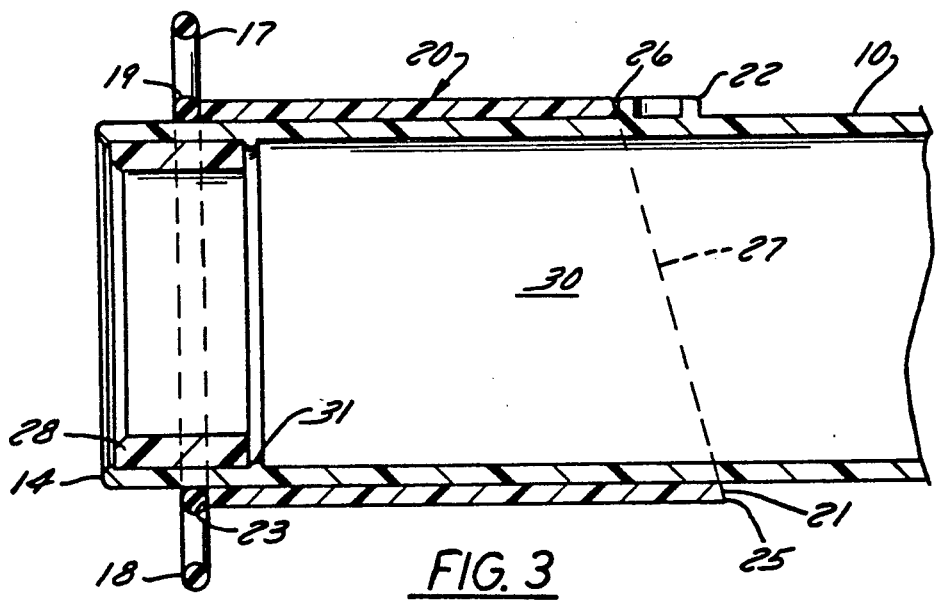
FIG. 3 is a partial longitudinal section taken through the distal end of a vacuum cylinder on which the new restrictor ring transfer sleeve is installed.

FIG. 3 shows a restrictor ring 19 installed on the open distal end rim 14 of vacuum cylinder 10. A penis size adapter 28 is inserted in the bore of cylinder 10 and is limited in its inward movement into the vacuum chamber 30 of cylinder 10 as a result of being stopped against a ridge 31 which is formed integrally within the bore of cylinder 10 when the plastic cylinder is molded. Thus, FIG. 3 depicts the vacuum apparatus in condition for being used to promote an erection.

Figure 4:
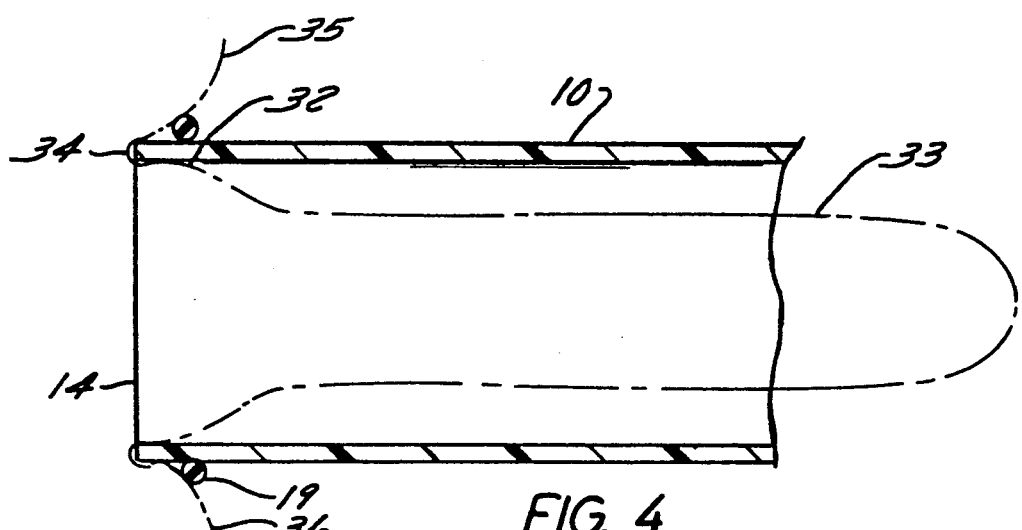
FIG. 4 depicts a section of the distal end of a vacuum cylinder representative of those used commonly in prior vacuum apparatus to depict how the restrictor ring becomes overlayed with soft tissue when the penis and tissue immediately surrounding its base is subjected to vacuum in the cylinder.

Refer now to FIG. 4 for a discussion of what happens in prior art vacuum therapy apparatus when the user is at the point where he must force the restrictor ring 19 from the distal end or rim 14 so that the restrictor ring 19 will slide off cylinder 10 and onto the base 32 of the penis of 33 approximately where the reference numeral 34 is applied. One may see that under vacuum conditions in the cylinder 10 the soft tissue 32 of the pubic area is pulled into the cylinder where the reference numeral 32 is applied. More distressing, however, is that the restrictor ring 19 must be pushed off of the distal end of the cylinder 10 by the user getting his fingers under the flabby tissue sections 35 and 36 which result from the end of the cylinder 10 being pressed into and drawn by vacuum into the soft tissue surrounding the base of the penis in the pubic area. This is the occasion for the user to experience pain and possible injury as a result of having to get his fingers under the soft tissue for the purpose of pushing the ring 19 from the cylinder 10 in prior art vacuum therapy apparatus. FIG. 7 shows a vacuum cylinder 10 equipped with the new restrictor ring applicator sleeve 20. The assumption in this case is that the vacuum has been created to cause the erection and bring about forming of a deep groove around the distal end rim 14 of cylinder 10 in the body tissue outlined by the dashed lines marked 35 and 36. The restrictor ring 19 is presently positioned slightly back from the distal end rim 14 of cylinder 10. The beveled camming surface 27 at the short side 26 of the applicator sleeve 20 is presently bearing against the cam or stop 22 which is fixed on the periphery of vacuum cylinder 10. This allows the square end 23 of sleeve 20 to retract from the rim 14. Assuming in FIG. 7 that the chamber 30 of cylinder 10 has been evacuated such as to cause the penis 33 to become erect as shown, the next step in the procedure is to rotate applicator sleeve 20 until the cam surface 27 and the long side 25 of the sleeve rotates into contiguity with the fixed stop or cam element 22. During rotation, sleeve 20 is driven axially towards a distal end 14 of the cylinder and the restrictor ring is pushed off as has been accomplished in FIG. 8.

Figure 8:
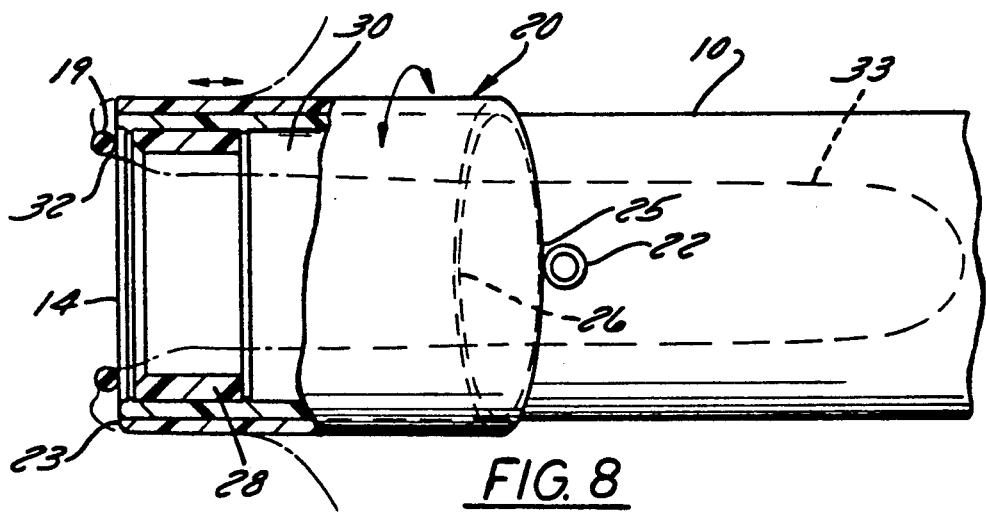
FIG. 8 is structurally similar to FIG. 7 except that the transfer sleeve has been rotated 180° to drive the restrictor ring off the outside diameter of the vacuum cylinder and onto the base of the penis.

In FIG. 8, the long side 25 of sleeve 20 is now riding on cam 22 and the sleeve is then advanced axially to the place where the restrictor ring 19 has dropped onto the base tissue of the penis. Now the vacuum can be relieved and the penis can be withdrawn from the cylinder 10 and the elastic force of ring 19 will prevent outflow of blood from the penis such as to preserve the erection for a recommended period of time of no greater than thirty minutes. Since the finger tips of the user never need to dig under the tissue in order to push or roll the ring 19 off of the cylinder, the transfer of the ring from the cylinder to the penis is not at all uncomfortable.

Figures 9, 10, 11:
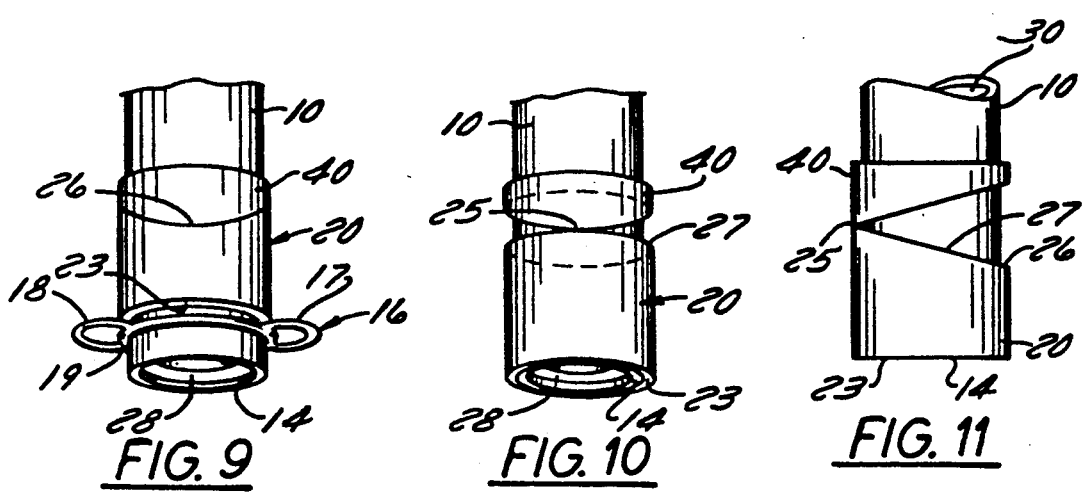
FIGS. 9–11 illustrate an alternative embodiment of the new restrictor ring applicator.

FIG. 9-11 depict a restrictor ring transfer device embodiment wherein the cam element is configured differently from cam element 22 in the preceding embodiment. In the FIGS. 9-11 embodiment, the restrictor ring transfer sleeve 20 is identical to sleeve 20 used in the previously discussed embodiment. As can be seen particularly well in FIG. 11, the fixed cam in this case comprises a plastic ring which fits tightly onto the periphery of vacuum cylinder 10 and is fixed thereon. This cam ring 40 has a beveled surface and in this case sleeve 20 is rotatable on the periphery of vacuum cylinder 10 as was the case in the previously described embodiment.

Figure 12:
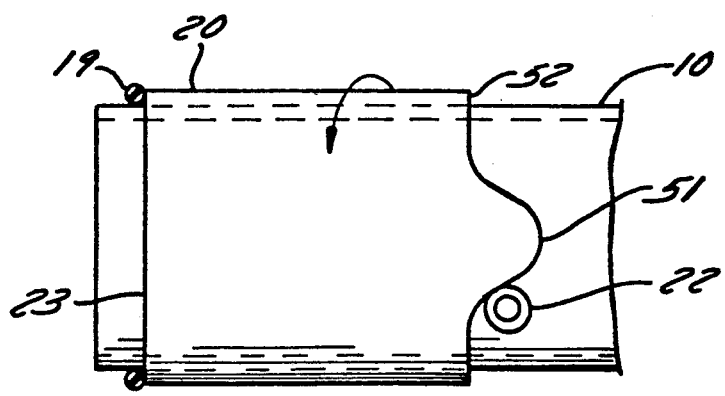
FIG. 12 depicts another modification of the restrictor ring applicator sleeve.

In the FIG. 12 modification of the sleeve, however, a circumferentially relatively short axially extending curved riser or camming surface 51 is formed on an end of the sleeve. As shown in FIG. 12, the sleeve 20 is assumed to be under rotation and advancing toward restrictor ring 19 by virtue of the curved riser riding along the fixed cam element 22. Of course, when the sleeve 20 is not rotated to an angular position wherein the crest of curved cam surface 51 is riding on cam stop 22, the square part 52 of the sleeve 20 will be allowed to retract axially to the right until it stops against the cam element 22. Under this condition, the sleeve will be retracted away from restrictor ring 19.

Another alternative form of transfer sleeve, not shown, but which conforms with the basic principles of the invention is one in which a helical slot is formed in a sleeve and in which a pin in the vacuum cylinder extends into the groove in the longitudinal wall of the sleeve. In such case, the pin is anchored to the periphery of the vacuum cylinder in a fashion such that it extends through the helical slot. Thus, when the sleeve is rotated, the sides of the slot ride on the cam pin such as to impel the sleeve in one axial direction or another. The sides of the slot act as the camming surface of the sleeve in this case.

Although various embodiments of the invention have been described in detail, such description is intended to be illustrative rather than limiting, for the invention may be variously embodied and is to be limited only by interpretation of the claims which follow.

I claim:

1. A device to assist maintaining an erect penis by applying a blood flow restrictor ring to the root of the penis, comprising:
    a hollow cylinder having an open end for receiving the penis and for effecting a seal with the anatomy surrounding the root of the penis, said cylinder having a region adjacent said open end for storing a restrictor ring circumjacent said cylinder,
    means for coupling said cylinder to a vacuum inducing source,
    a cam element fixed on the periphery of said cylinder at a predetermined distance from said open end,
    a sleeve member slidable axially and rotatable on the periphery of said cylinder, said sleeve member having a first end presented toward said region for storing said restrictor ring and having a second end,
    said second end having an axially projecting cam riser such that when said sleeve member is rotated with said riser running on said cam element said sleeve member moves axially for said first end thereof to push said restrictor ring from the cylinder and onto the root of the penis.

2. The device according to claim 1 wherein said cam element is a riser which is unitary with said cylinder.

3. The device according to claim 1 wherein said cam element comprises a tubular member fixed on the periphery of said cylinder, said tubular member having an angulated camming rim and said second end of the sleeve member having an angulated rim corresponding to the angulation of said camming rim such that when said sleeve member is rotated with the angulated rim thereof in contact with said rim of the tubular member said sleeve member advantages and retracts axially of the cylinder.

4. A device for applying a blood flow restriction ring to the root of the male penis, comprising:
    a hollow evacuable cylinder for retaining on an area of its periphery adjacent an opening in the end of the cylinder a restriction ring for being slid off the cylinder and onto the root of the penis when the penis is in the cylinder and the end of the cylinder is held proximate to the anatomy surrounding the root of the penis,
    a cam follower element fixed to the periphery of the cylinder at a predetermined distance from the end of the cylinder,
    a cylindrical sleeve member axially slidable and rotatable on the periphery of said cylinder between said cam follower element and said area for retaining the restriction ring, said sleeve member having a first end presented toward said area on the cylinder and a second end presented toward said cam follower element,
    said second end of the sleeve member terminating in an angulated camming rim defined by a plane which is angulated relative to the axis of the cylindrical sleeve such that rotation of said sleeve on said cylinder with said angulated rim in contact with said cam follower element to one position retracts said sleeve member axially to accommodate said restriction ring and rotation to another position advances said sleeve member axially for sliding said restriction ring off the cylinder and onto the root of the penis, and
    means for coupling said hollow cylinder to a source of vacuum.

* * * * *

UNITED STATES PATENT AND TRADEMARK OFFICE
CERTIFICATE OF CORRECTION

PATENT NO. : 5,195,943
DATED : March 23, 1993
INVENTOR(S) : John L. Chaney

It is certified that error appears in the above-indentified patent and that said Letters Patent is hereby corrected as shown below:

Column 6, line 34 "advantages" should be ---advances---.

Signed and Sealed this

Twenty-ninth Day of March, 1994

Attest:

BRUCE LEHMAN

Attesting Officer     Commissioner of Patents and Trademarks